(12) United States Patent  (10) Patent No.: US 9,179,989 B2
Mullaly  (45) Date of Patent: Nov. 10, 2015

(54) O-RING INSERTION TOOL AND METHOD

(75) Inventor: Scott Mullaly, San Marcos, CA (US)

(73) Assignee: ZEST IP HOLDINGS, LLC, Escondido, CA (US)

( * ) Notice: Subject to any disclaimer, the term of this patent is extended or adjusted under 35 U.S.C. 154(b) by 451 days.

(21) Appl. No.: 12/822,852

(22) Filed: Jun. 24, 2010

(65) Prior Publication Data

US 2010/0330536 A1  Dec. 30, 2010

Related U.S. Application Data

(60) Provisional application No. 61/220,086, filed on Jun. 24, 2009.

(51) Int. Cl.
*A61C 13/265* (2006.01)
*B25B 27/00* (2006.01)

(52) U.S. Cl.
CPC ......... *A61C 13/2656* (2013.01); *B25B 27/0028* (2013.01)

(58) Field of Classification Search
CPC ............ A61C 13/2656; B25B 27/0028; Y10T 29/53657
USPC ............ 433/2–3, 24, 141, 163, 215, 229; 29/222, 235, 255, 451
See application file for complete search history.

(56) References Cited

U.S. PATENT DOCUMENTS

| | | | | |
|---|---|---|---|---|
| 3,180,015 A | * | 4/1965 | Thompson et al. | 29/235 |
| 3,289,286 A | * | 12/1966 | Belanger | 29/235 |
| 3,412,897 A | * | 11/1968 | Slater | 221/226 |
| 4,005,883 A | * | 2/1977 | Guest | 285/322 |
| 4,106,374 A | * | 8/1978 | Dragan | 81/302 |
| 4,141,129 A | * | 2/1979 | Martini | 29/235 |
| 4,203,191 A | * | 5/1980 | Gibson, Sr. | 29/451 |
| 4,719,684 A | * | 1/1988 | Mutter | 29/235 |
| 5,050,282 A | * | 9/1991 | Zannini | 29/235 |
| 5,054,647 A | * | 10/1991 | Yawata | 221/41 |
| 5,138,752 A | * | 8/1992 | Tasner | 29/235 |
| 5,387,389 A | * | 2/1995 | Catalanotti et al. | 264/318 |
| 5,862,578 A | * | 1/1999 | Castleman | 29/235 |
| 5,956,830 A | * | 9/1999 | Imbus et al. | 29/235 |
| 6,012,209 A | * | 1/2000 | Whetstone | 29/235 |
| 6,108,884 A | * | 8/2000 | Castleman et al. | 29/235 |
| 6,257,887 B1 | * | 7/2001 | Heckerman et al. | 433/141 |
| 6,397,446 B1 | * | 6/2002 | Whetstone | 29/235 |
| 6,722,011 B1 | * | 4/2004 | Bacon | 29/451 |
| 6,993,816 B2 | * | 2/2006 | Greenhill | 29/229 |

* cited by examiner

*Primary Examiner* — Cris L Rodriguez
*Assistant Examiner* — Hao D Mai
(74) *Attorney, Agent, or Firm* — Procopio, Cory, Hargreaves & Savitch LLP; Noel C. Gillespie

(57) ABSTRACT

An O-ring insertion tool is disclosed herein which holds and inserts an O-ring into a cap for releasably securing a dental appliance to, for example, a dental attachment assembly secured in the mouth of a patient. The tool contains a driver having a central portion and at least one end portion with resilient prongs designed to push an O-ring through a bore in a bushing sleeve sized at one end to match the entrance of the cap. The bore has a tapered, frustoconical portion. The prongs fit into the larger end of the bore in which the O-ring is positioned and engage and advance the O-ring through the bore. The O-ring is uniformly compressed as it advances through the frustoconical portion of the bore, and is then pushed out of the second end of the bore and into position in the cap.

12 Claims, 5 Drawing Sheets

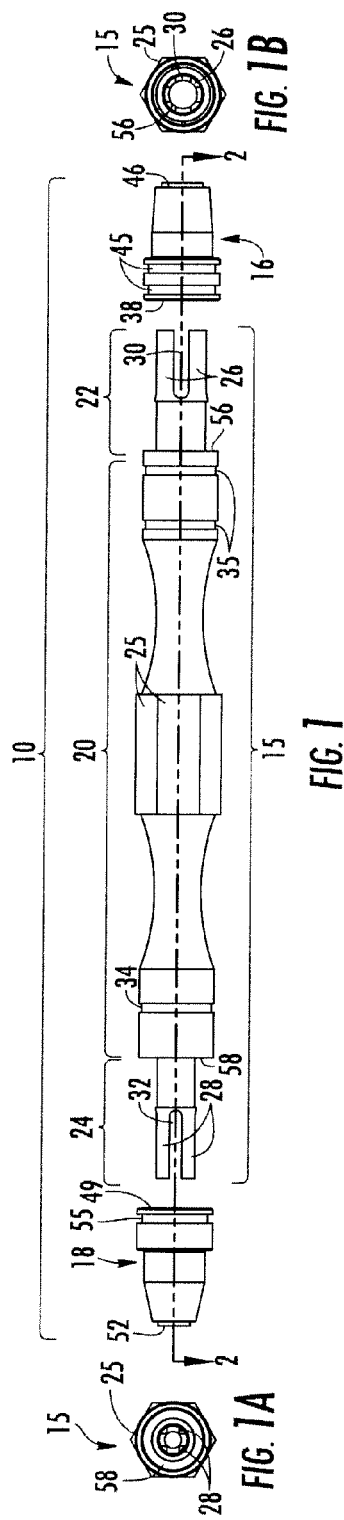
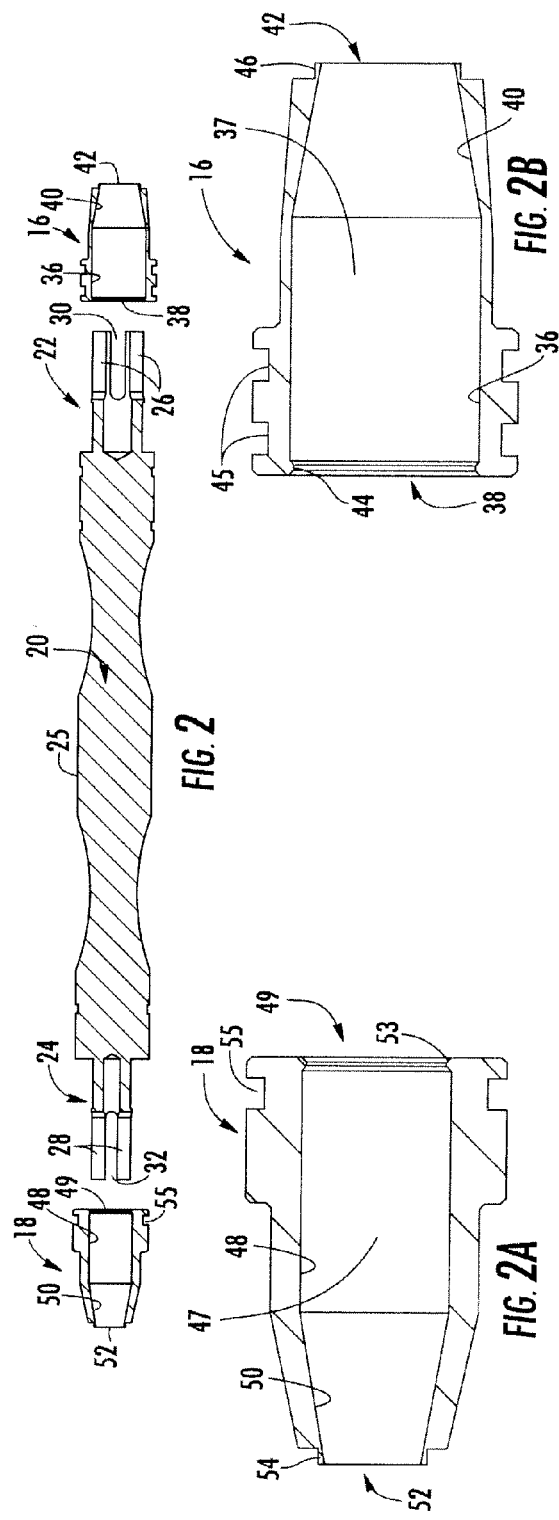

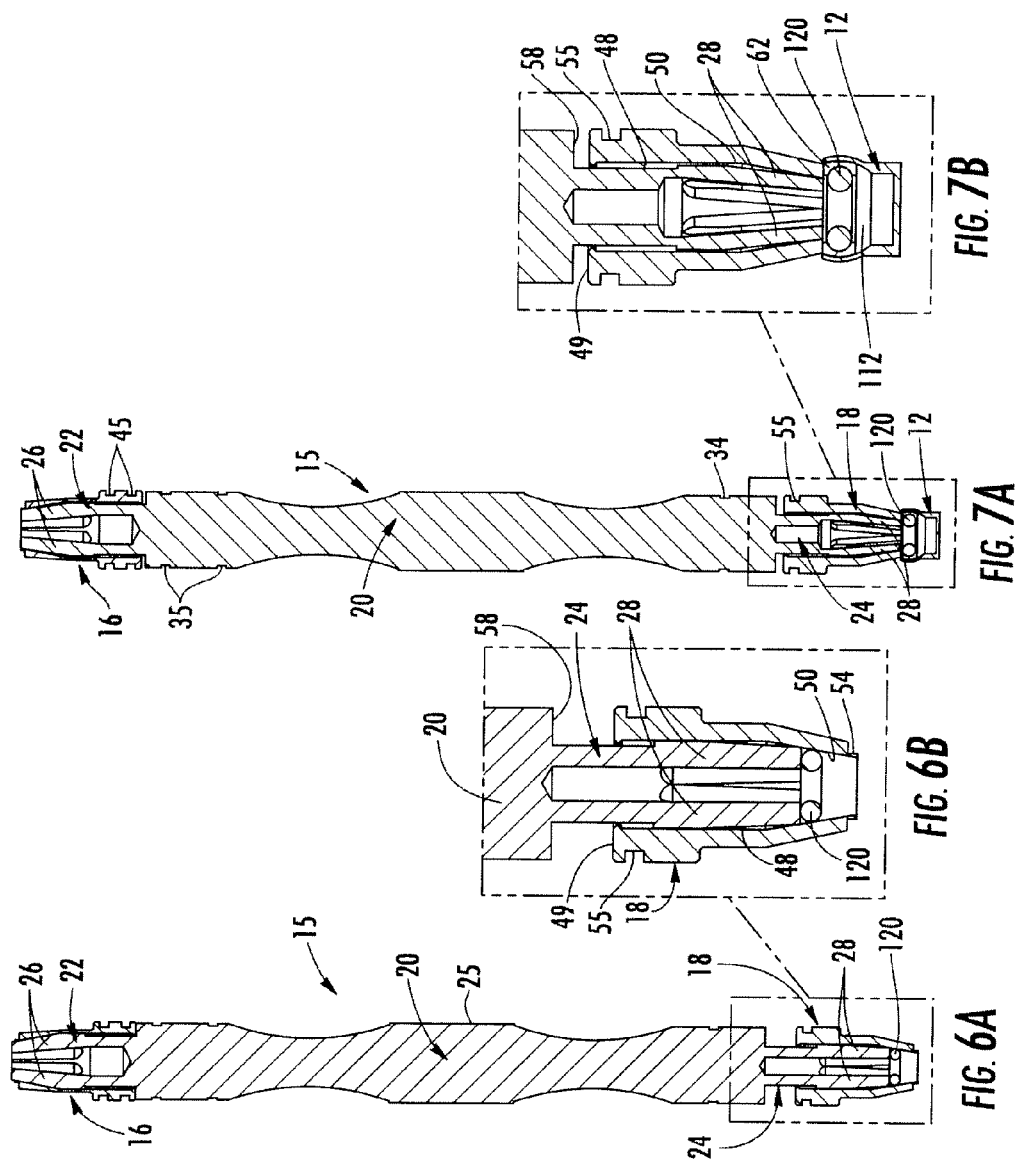

US 9,179,989 B2

O-RING INSERTION TOOL AND METHOD

FIELD

An apparatus and method for inserting an O-ring into a cap for securing a dental appliance, for example, via a dental attachment system, in the mouth of a patient.

BACKGROUND

Various systems and methods are known for attaching a dental prosthesis, such as a full or partial denture or the like, in the mouth of a patient. Such systems generally comprise mating male and female parts, one of which is attached to the dental prosthesis and the other to an abutment which is mounted at a selected position in the patient's jaw. The abutment may be attached to a root, an endosseous implant, or an adjacent tooth, or in some cases, may be integrated directly into the jaw bone of the patient.

One known attachment uses an O-ring or plastic ring member which is inserted and retained in a cap which is secured in a recess in a dental prosthesis. The O-ring engages over a ball at the end of an implant abutment or post to releasably secure the denture in place in a patient's mouth. One example of this type of attachment is described in U.S. Pat. No. 6,716,030 of Bulard et al. One problem with this type of attachment is the difficulty associated with the initial placement of the O-ring into the cap and the subsequent replacement of the O-ring when it becomes damaged or worn from repeated removal and re-attachment of the denture. The O-ring has to compress evenly as it is inserted into the cap, but it has the tendency to spring back out if this is not done correctly. The dimensions of the O-ring and cap are such that it is very difficult to insert the O-ring by hand or with tweezers, which is the current method.

Accordingly, there is a need in the art for a faster and more efficient tool and/or method of inserting an O-ring into a cap.

SUMMARY

Described herein is a tool designed to hold and insert an O-ring into a cap which is integral with a dental prosthesis. The cap may be part of, for example, a dental attachment system for securing the dental prosthesis in the mouth of a patient.

In one embodiment, an O-ring insertion tool is provided which comprises a driver, which has a handle or gripping portion and at least one driving end portion, and at least one bushing sleeve having opposite first and second ends and a bore extending therethrough from the first end to the second end which is tapered along at least part of its length. The first end of the bore is shaped to receive an O-ring intended for insertion in a cap component, for example, of a denture attachment assembly. The driving end portion of the driver is adapted to engage in the first end of the bore of the sleeve and move the O-ring through the bore so that the O-ring is compressed as it advances through the tapered portion of the bore. In a further embodiment, the second end of the sleeve has a lip for engagement with the open end of a cap aligned with the sleeve and driver. In another embodiment, the second end of the sleeve has a chamfered end for engagement with the open end of the cap. The driving end portion of the driver is further adapted to push the O-ring out of the open second end of the bore and into position in the cap.

Other embodiments, objects, features and advantages will be set forth in the detailed description of the embodiments that follows, and in part will be apparent from the description, or may be learned by practice, of the claimed invention. These objects and advantages will be realized and attained by the apparatus and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 1 is a side view of the O-ring insertion tool;

FIG. 1A is an end view of the left-hand end of the driver of FIG. 1;

FIG. 1B is an end view of the right-hand end of the driver of FIG. 1;

FIG. 2 is a cross-sectional view of FIG. 1;

FIG. 2A is an enlarged cross-sectional view of the smaller bushing sleeve of FIG. 2;

FIG. 2B is an enlarged cross-sectional view of the larger bushing sleeve of FIG. 2;

FIG. 6A is a cross-sectional view of the driver illustrating the prongs at one end of the driver engaging in the bushing sleeve and pushing the O-ring through the bore of the sleeve;

FIG. 6B is an enlarged view of the indicated portion of FIG. 6A;

FIG. 7A is a cross-sectional view of the O-ring pushed out of the sleeve and into position in an aligned cap;

FIG. 7B is an enlarged view of the indicated portion of FIG. 7A;

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated and/or described. The headings used throughout this disclosure are provided for convenience only and are not to be construed to limit the claims in any way. Embodiments illustrated under any heading may be combined with embodiments illustrated under any other heading.

The various embodiments disclosed and described herein provide for a tool which inserts an O-ring into position in a cap which may be integral with a dental prosthesis as part of a denture attachment assembly. Also described herein is a method of using the tool to install O-rings of different dimensions in different size caps.

Figure 8:
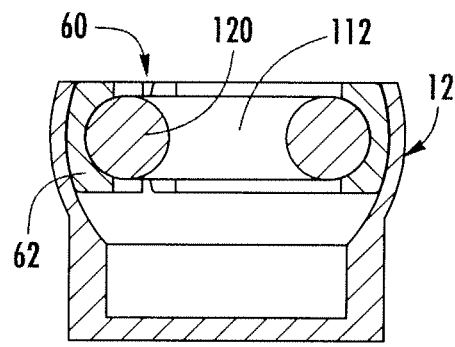
FIG. 8 is an enlarged cross-sectional view of the cap after an O-ring is positioned therein.
Figure 9:
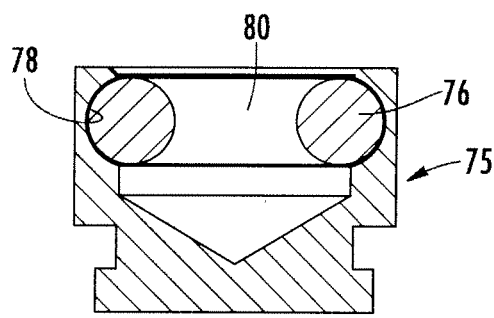
FIG. 9 is a cross-sectional view of another embodiment of the cap with an O-ring positioned therein.
Figure 10:
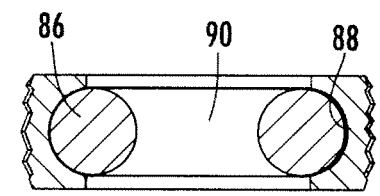
FIG. 10 is a cross-sectional view of a knurled O-ring cap with an O-ring positioned therein.

FIGS. 1 to 3 illustrate one embodiment of a O-ring insertion tool 10, and FIGS. 4 to 7B illustrate one embodiment of a method for inserting an O-ring 120 into a cap 12 for securing a dental prosthesis using the tool 10. FIGS. 8 to 10 illustrate additional embodiments of caps 12, 75 and 85 with which the tool 10 may be used. In one embodiment, the tool 10 comprises an elongated driver 15, a large bushing sleeve or cone 16, which engages one end of the driver, and a small bushing sleeve or cone 18, which engages the opposite end of the driver. The driver and two cones may be made of the same material, and in one embodiment, each part can be formed from a thermoplastic polymer material, such as polysulphone, which is relatively strong, temperature resistant, and autoclavable, so that the driver and cones are resistant to repeated sterilizations after use.

Referring to FIGS. 1 and 2, the driver 15 is a post-like member having a central handle portion 20 and opposite driving end portions 22 and 24. In one embodiment, the end portion 22 has a larger cross-sectional dimension than the end portion 24. The disclosure of this embodiment should not be read to limit the shape of the driver 15. Rather, the driver can be any shape suitable to handle the tool with at least one driving end portion. The sizes of end portions 22 and 24 are chosen for mating engagement with the respective sleeves or cones 16 and 18 and described in more detail below. A central region of the central handle portion 20 can be substantially a polygonal shape to provide flats 25 so that the tool 10 does not tend to roll when placed on a flat surface. Each end portion 22 and 24 has an O-ring engaging member 26 and 28 for moving the O-ring through the respective cones 16 and 18 and into the cap 12 of FIG. 7B. In one embodiment, the O-ring engaging member 26 and 28 is a series of spaced prongs or fingers that extend outward from each respective end of the driver and are separated by gaps 30 and 32, respectively. The prongs are resilient to allow for elastic deformation of the prongs. There are four equally spaced prongs in the illustrated embodiment of FIGS. 1A and 1B. In further embodiments, there may be fewer than, or more than four prongs, such as three prongs, five prong, six prongs, seven prongs and eight prongs or more. Although the O-ring engaging member 26 and 28 is shown as prongs in FIG. 1, alternative embodiments of the O-ring engaging member 26 and 28 are also contemplated to be within the scope of the present disclosure. There is a slight undercut 29 on the outer surface, shown in FIG. 3B) adjacent to the end of each prong and described in more detail below in association with FIG. 3B. In one embodiment, the central portion 20 of the driver 15 has a single groove 34 close to the smaller end portion 24 and a pair of grooves 35 near the larger end portion 22.

Figure 11:
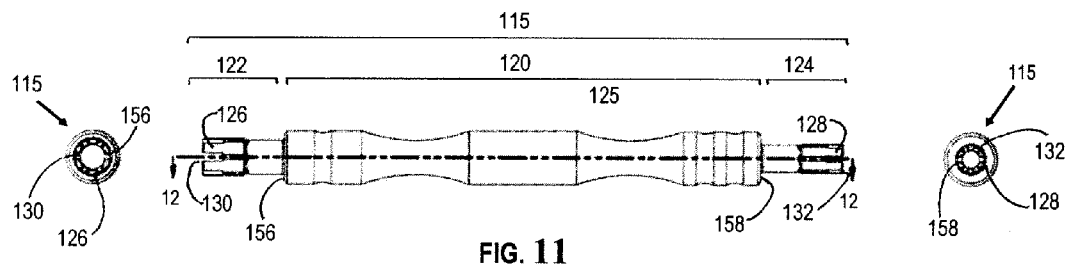
FIG. 11 is a side view of another embodiment of the O-ring insertion tool.
Figure 12:
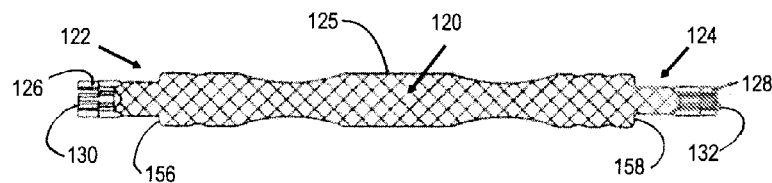
FIG. 12 is a cross-sectional view of FIG. 11.

FIGS. 11 and 12 illustrate another embodiment of the O-ring insertion tool. The O-ring insertion tool is similar to that of the previous embodiment described in connection with FIGS. 1 and 2 apart from the O-ring engaging portions 126 and 128, and like reference numerals have been used for like parts. In one embodiment, the tool comprises an elongated driver 115, a large bushing sleeve or cone 116, which engages one end of the driver, and a small bushing sleeve or cone 118, which engages the opposite end of the driver. Referring to FIGS. 11 and 12, the driver 115 is a post-like member having a central handle portion 120 and opposite driving end portions 122 and 124. In one embodiment, the end portion 122 has a larger cross-sectional dimension than the end portion 124. The disclosure of this embodiment should not be read to limit the shape of the driver 115. Rather, the driver can be any shape suitable to handle the tool with at least one driving end portion. The sizes of end portions 122 and 124 are chosen for mating engagement with the respective sleeves or cones 116 and 118 (shown in FIGS. 13A and 13B). A central region of the central handle portion 120 can be substantially a polygonal shape to provide flats 125 so that the tool does not tend to roll when placed on a flat surface. Each end portion 122 and 124 has an O-ring engaging member 126 and 128 for moving the O-ring through the respective cones 116 and 118 and into the cap 12. In one embodiment, the O-ring engaging member 126 and 128 is a series of six spaced prongs or fingers that extend outward from each respective end of the driver and are separated by gaps 130 and 132, respectively. In further embodiments, there may be fewer than, or more than six prongs, such as three prongs, four prong, five prongs, seven prongs and eight prongs or more. The prongs are resilient to allow for elastic deformation of the prongs. Although the O-ring engaging member 126 and 128 is shown as prongs in FIGS. 11 and 12, alternative embodiments of the O-ring engaging member 126 and 128 are also contemplated to be within the scope of the present disclosure In one embodiment illustrated in FIGS. 2 and 2B, the larger cone or sleeve 16 has a bore 37 extending axially along the length of the cone or sleeve 16 and in one embodiment has an optional first portion 36 of uniform diameter extending from a first end 38 and a second tapering portion 40 which extends up to a second end 42. In a further embodiment, the tapering portion 40 has a frustoconical shape or other tapering shape that assists in compressing the O-ring as it moves from the first end 38 to the second end 42 of the cone 16. The second portion 40 of the cone 16 can be coated with a low friction material, such as Teflon® or other suitable material, in order to reduce friction between the O-ring and the tapered surface of the second portion 40. A small annular rib 44 is located at the first end 38 of the bore 37. In one embodiment, a pair of annular grooves 45 is provided on the outer surface of the cone 16 in the vicinity of the first end 38. In a further embodiment, a lip or rim 46 of reduced diameter projects outwardly from the second end 42 of the cone 16.

Referring to FIG. 2A, the smaller cone or sleeve 18 is of similar shape but smaller dimensions than cone 16 and also has a bore 47 extending axially along the length of the cone or sleeve 18 and in one embodiment has an optional first portion 48 of uniform diameter extending from a first end 49 and a second tapering portion 50 which extends up to a second end 52. In a further embodiment, the tapering portion 50 has a frustoconical shape or other tapering shape that assists in compressing the O-ring as it moves from the first end 49 to the second end 52 of the cone 18. The second portion 50 of cone 18 can be coated with a low friction material, such as Teflon® or other suitable material, in order to reduce friction between the O-ring and the tapered surface of the second portion 50. A small annular rib 53 is provided at the first end 49 of the cone and in a further embodiment a reduced diameter lip 54 projects outwardly from the second end 52. In one embodiment, cone 18 has a single annular groove 55 adjacent the first end 49, rather than a pair of grooves 45 as on the larger cone 16. In another embodiment, the cones are each of transparent material so that the user can easily view an O-ring being pushed from the cone or sleeve 16 or 18 and into an aligned cap, as discussed in more detail below.

Figures 13A, 13B:
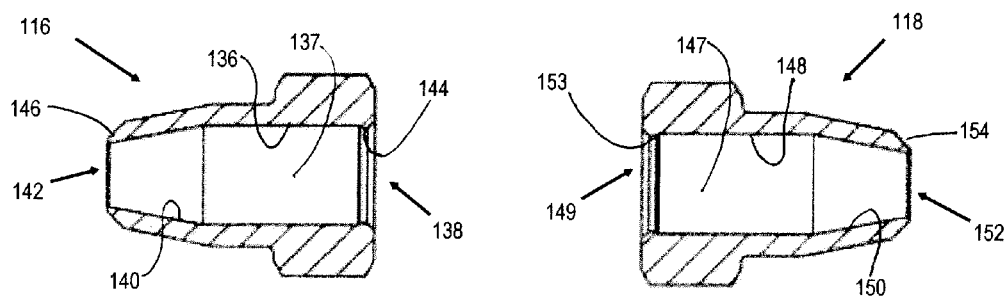
FIG. 13A is a cross-sectional view of a small bushing sleeve with a chamfered end.
FIG. 13B is a cross-sectional view of a large bushing sleeve with a chamfered end.

A further embodiment of the sleeve or cone is illustrated in FIGS. 13A and 13B. The sleeves or cones 116 and 118 are similar to that of the previous embodiments described in connection with FIGS. 2A and 2B apart from the chamfered end 146 and 154 at the respective second ends 142 and 152 of the cones 116 and 118, respectively, and like reference numerals have been used for like parts. In one embodiment illustrated in FIG. 13B, the larger cone 116 has a bore 137 extending axially along the length of the cone or sleeve 116 and in another embodiment has an optional first portion 136 of uniform diameter extending from a first end 138 and a second tapering portion 140 which extends up to a second end 142. In a further embodiment, the tapering portion 140 has a frustoconical shape or other tapering shape that assists in compressing the O-ring as it moves from the first end 138 to the second end 142 of the cone 116. The second portion 140 of the cone 116 can be coated with a low friction material, such as Teflon® or other suitable material, in order to reduce friction between the O-ring and the tapered surface of the second portion 140. The second end 142 has a chamfered end 146 to mate with the cap 12.

Similarly, as illustrated in FIG. 13A, the smaller cone 118 has a bore 147 extending axially along the length of the cone or sleeve 118 and in one embodiment has an optional first portion 148 of uniform diameter extending from a first end 149 and a second tapering portion 150 which extends up to a second end 152. In one embodiment, the tapering portion 150 has a frustoconical shape or other tapering shape that assists in compressing the O-ring as it moves from the first end 149 to the second end 152 of the cone 118. The second portion 150 of cone 118 can be coated with a low friction material, such as Teflon® or other suitable material, in order to reduce friction between the O-ring and the tapered surface of the second portion 150. A small annular rib 153 is provided at the first end 149 of the cone. In a further embodiment, the second end 152 of the cone 118 has a chamfered end 154.

Figure 3A:
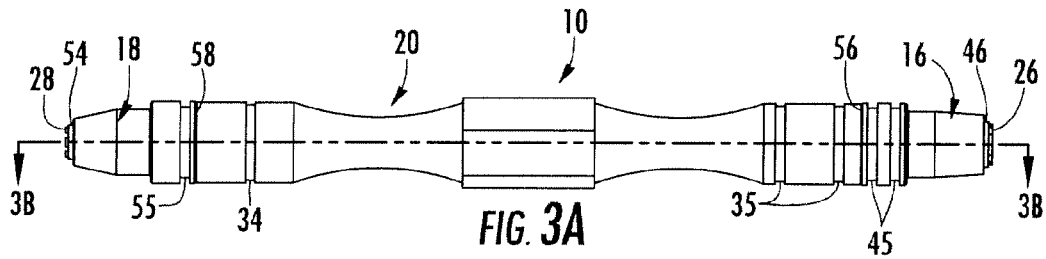
FIG. 3A is a side view of the two bushing sleeves engaged on opposite end portions of the driver.
Figure 3B:
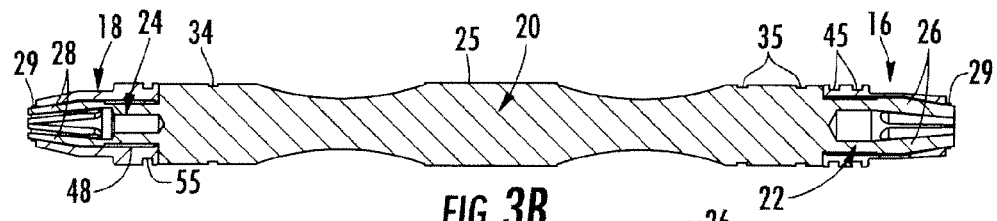
FIG. 3B is a cross-sectional view of FIG. 3A.

When the tool is not in use, the cones 16 and 18 are stored on the respective driving end portions 22 and 24 of the driver, as illustrated in FIGS. 3A and 3B. In one embodiment, the user can easily match the cone with the proper end of the driver, since the smaller cone and smaller end of the driver both have one outer groove 55 and 34, respectively, while the larger cone and the larger end of the driver both have two outer grooves 45 and 35, respectively. The larger first ends 38 and 49 of the two cones 16 and 18, respectively, are each engaged over the respective O-ring engaging members 26 and 28. In one embodiment, the O-ring engaging members 26 and 28 can be, but is not limited to, one or more prongs. However, the disclosure of this embodiment should not be understood to limit the shape of the O-ring engaging member. Rather, the O-ring engaging member can be of any shape suitable to advance the O-ring though the cone or sleeve 16 and 18 and into a cap 12 as described in detail below. Each cone 16 or 18 is engaged with its respective driving end portion 22 or 24 until the respective first ends 38 or 49 of each cone abuts a respective annular shoulders 56 or 58 located between the driving end portion and the central portion 20. The diameter of the driving end portion 22 is slightly less than the diameter of the first end 38 of the cone 16. Similarly, the diameter of driving end portion 24 is slightly less than the diameter of the first end 49 of the cone 18. In one embodiment, the O-ring engaging members 26 and 28 are in the form of prongs which are inserted and advanced along the respective bore 37 or 47. They are elastically deformed or flexed inwardly as they move through the tapered portions 40 and 50, respectively. In the fully engaged position of FIGS. 3A and 3B, the tip of each prong projects out of the second end 42 and 52 of cones 16 and 18, respectively, and the undercuts 29 engage over the end face of the respective cone, releasably retaining the cone 16 and 18 on the respective driving end portion 22 and 24 until a user wishes to use the O-ring insertion tool 10. The undercuts 29 are sufficiently small that a user can pull the cones 16 and 18 off the respective end portions 22 and 24 when desired, yet help to prevent the cones 16 and 18 from being forced off the end portions 22 and 24 due to the spring pressure of the inwardly deformed prongs.

When a worn O-ring needs to be replaced, the old O-ring is first removed from the cap and a proper size new O-ring is selected to replace it. FIG. 8 is an enlarged view of a cap 12 to be secured in a recess in a dental prosthesis and forming part of, for example, an attachment assembly for releasably securing the dental prosthesis in the mouth of a patient. In one embodiment, the cap has an open-ended cavity 112 for receiving the O-ring 120 and in which the head of an abutment is snap engaged. The abutment may be secured to a tooth, tooth root, implant or directly into the jaw bone of a patient. The head of the abutment snaps through an O-ring 120 held in a retainer ring 62 which is in swivel engagement in the cavity 112. The user determines which end of the tool 10 matches the O-ring 120, and the cone 16 or 18 is removed from that end of the driver 15. The user proceeds to insert the O-ring 120 into the cap 12 using the selected cone 16 or 18 and driver 15 as described below.

Figure 4:
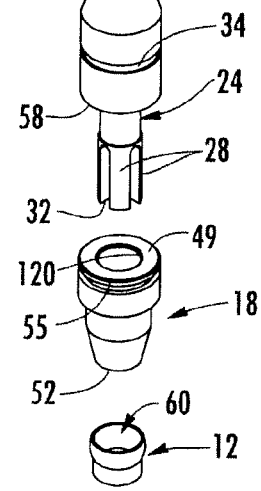
FIG. 4 is a perspective view of one of the bushing sleeves aligned with an O-ring prior to engagement over the O-ring.

In FIG. 4, the larger cone 16 has been removed and is aligned vertically over an O-ring 120 that is placed on a suitable flat support surface with the first end 38 of the cone 16 facing downward and toward the O-ring 120. The cone 16 is then pushed down over the O-ring 120 until the O-ring 120 is slightly compressed and the rib 44 (shown in FIG. 2B) snaps over the O-ring 120. The O-ring 120 is then retained in the larger first end 38 of the cone 16. The same procedure can be carried out for a smaller O-ring 120 matching the smaller cone 18 and smaller driving end portion 24 of the driver 15.

Figure 5:
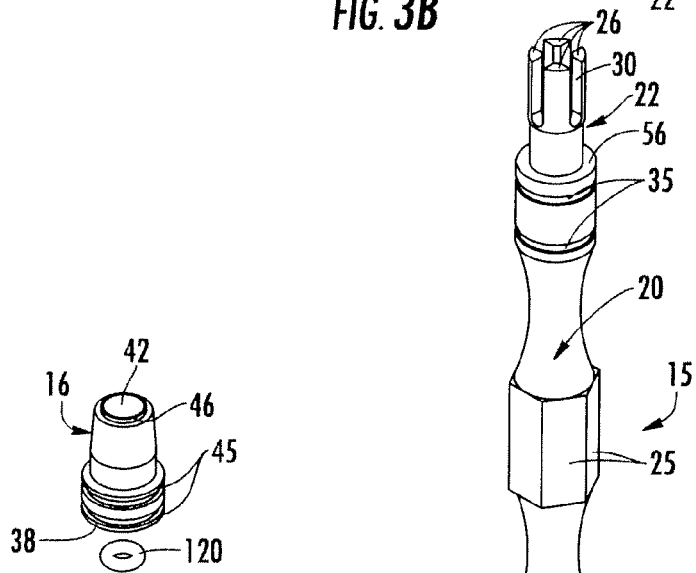
FIG. 5 is a perspective view of the driver with the prongs at one end of the driver aligned with the open end of the bushing sleeve which is holding the O-ring and with a cap into which the O-ring is to be inserted.

Referring to FIG. 5, the second end 52 of cone 18 with the O-ring 120 retained in the first end 49 is aligned with the open end 60 of cap 12 and the driving end portion 24 of the driver 15 is aligned with the first end 49 of the cone 18. The O-ring engaging member 28 at the driving end portion 24 engages the first end 49 so that the front end of the O-ring engaging member 28 engages the O-ring 120 and advances the O-ring 120 through the bore 37 of cone 18. As illustrated in FIGS. 6A and 6B, as the O-ring enters the tapered second portion 50 of the bore 37, the O-ring 120 is compressed while the tips of the O-ring engaging member 28 are similarly deformed inwardly so that they continue to engage the O-ring 120. In one embodiment, the user can see the location of the O-ring 120 in the cone since the cone walls can be transparent. When the cone 18 is in a loaded position, i.e., the O-ring is close to the second end 52 of the cone 18, the second end 52 is placed at the open end 60 of the cap 12 with the lip 54 mating with the open end 60 of cap 12. As illustrated in FIGS. 7A and 7B, the O-ring engaging members 28 push the O-ring out of the cone 18 and into the cap 12. At this point, the cone 18 is retained on the driving end portion 24 and the tool 10 can be removed from the cap 12, leaving the new O-ring 120 in position in the retainer ring 62 (shown in FIG. 8). The same procedure can be carried out for larger O-rings in the larger cone 16 using the larger end portion 22 of the driver.

In another embodiment, the method described above may also be used to insert an O-ring 76 into a standard cap 75 as illustrated in FIG. 9. The O-ring 76 is positioned in an annular seating groove 78 in the cap cavity 80 using the O-ring insertion tool 10. In yet a further embodiment illustrated in FIG.

10, the method may be used to insert an O-ring 86 in an annular seating groove 88 in the cap cavity 90 of a knurled O-ring cap 85.

The tool and insertion method described above allows for the quick and easy installation of O-rings in a cap which may be integral with a dental prosthesis, such as the O-rings in the dental attachment assembly described in co-pending U.S. patent application Ser. No. 11/613,464 filed on Dec. 20, 2006, the contents of which are incorporated herein by reference. The current method used to install such O-rings is to grasp the O-ring with fingers or tweezers and try to force it into the cap, which is very difficult since the compressed O-ring has the tendency to spring back out of the cap. The time needed to install a new O-ring may be reduced to as little as a few seconds when using the insertion tool and method described in the above embodiments.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein are representative of the subject matter which is broadly contemplated by the present invention. It is further understood that the scope of the present invention is not intended to be limited to the embodiment shown herein but is to be accorded the widest scope consistent with the principles and novel features disclosed herein.

All references, including publications, patent applications, and patents, cited herein are hereby incorporated by reference to the same extent as if each reference were individually and specifically indicated to be incorporated by reference and were set forth in its entirety herein.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

I claim:

1. A tool for inserting an O-ring into a dental prosthesis cap comprising:
    a driver comprising a first driving end portion having an O-ring engaging member extending outwardly from the first driving end portion; and
    a bushing sleeve having a first end, a second end and a bore extending therethrough from the first end to the second end, said bore having an inner surface, wherein the first end of the bushing sleeve has an annular inner rib extending radially from said inner surface for loading an and retaining the O-ring in the first end of the bushing sleeve, and wherein said inner surface having a first cylindrical portion at the first end and a second tapered portion at the second end;
    wherein the O-ring engaging member is configured to be inserted into the first end of the bushing sleeve to engage the loaded and retained O-ring which is to be inserted into the dental prosthesis cap, and wherein the O-ring engaging member moves relative to the inner surface of the bore and deforms inwardly as the O-ring engaging member moves in a direction from the first end to the second end of the bushing sleeve.

2. The tool of claim 1, wherein the driver is substantially post-shaped having a first distal end and a second distal end opposite from the first distal end.

3. The tool of claim 2, wherein the first driving end portion is disposed at the first distal end; and wherein the driver further comprises a second driving end portion disposed at the second distal end.

4. The tool of claim 1, wherein the O-ring engaging member has three prongs.

5. The tool of claim 1, wherein the O-ring engaging member has four prongs.

6. The tool of claim 1, wherein the O-ring engaging member has five prongs.

7. The tool of claim 1, wherein the O-ring engaging member has six prongs.

8. The tool of claim 1, wherein the bushing sleeve is formed of a transparent, thermoplastic polymer material.

9. The tool of claim 1, wherein the bushing sleeve has an annular lip extending from the second end of the bushing sleeve, the annular lip having an outer diameter less than an outer diameter of the second end of the bushing sleeve.

10. The tool of claim 1 wherein the second end of the bushing sleeve has a chamfered end.

11. A method of inserting an O-ring into a dental prosthesis cap for securing a dental prosthesis to a dental attachment assembly using the tool of claim 1, comprising the steps of:
   (a) loading the O-ring into the first cylindrical portion at the first end of the bushing sleeve past the annular inner rib, wherein the O-ring is retained by the annular inner rib at the first end of the bushing sleeve;
   (b) aligning the O-ring engaging member of the driver with the first cylindrical portion at the first end of the bushing sleeve;
   (c) inserting the O-ring engaging member of the driver into the first cylindrical portion at the first end of the bushing sleeve such that the O-ring engaging member engages the O-ring;
   (d) advancing the O-ring through the second tapered portion at the second end of the bushing sleeve where the O-ring is compressed;
   (e) aligning the second end of the bushing sleeve over the dental prosthesis cap; and
   (f) ejecting the O-ring from the second end of the bushing sleeve and into the dental prosthesis cap.

12. A method of inserting an O-ring into a cap for securing a dental prosthesis to a dental attachment assembly comprising the steps of:
   (a) selecting a bushing sleeve having a first end, a second end and a bore extending therethrough from the first end to the second end, wherein the bore has an inner surface having a first cylindrical portion at the first end, a second tapered portion at the second end, and an annular inner rib extending radially therefrom the inner surface at the first end;
   (b) loading and positioning the O-ring into the first end of the bushing sleeve past the annular inner rib which retains the O-ring in the first end of the bushing sleeve;
   (c) engaging a driver with the first end of the bushing sleeve, wherein the driver comprises a first driving end portion having an O-ring engaging member extending outwardly from the first driving end portion to engage the O-ring positioned in the first end of the bushing sleeve;
   (d) advancing the O-ring through the bore from the first end towards the second end with the O-ring engaging member whereby the O-ring is compressed and the O-ring engaging member deforms inwardly as the O-ring engaging member moves in a direction from the first end to the second end of the bushing sleeve;
   (e) aligning the second end of the bushing sleeve over the cap; and
   (f) ejecting the O-ring from the second end of the bushing sleeve and into the cap.

* * * * *